United States Patent
Peemans et al.

(10) Patent No.: US 6,680,270 B2
(45) Date of Patent: Jan. 20, 2004

(54) REGENERATION OF CATALYSTS USED IN THE MANUFACTURE OF BISPHENOLS

(75) Inventors: Rudy Francois Alain Joseph Peemans, Erps-Kwerps (BE); Alexey Kruglov, Evansville, IN (US); Sheldon Jay Shafer, Clifton Park, NY (US); Chuks O. Mbeledogu, Newburgh, IN (US); Darlene Hope Nance, Mount Vernon, IN (US); Karl Aaron Baro, Evansville, IN (US); Emil Markov Georgiev, Evansville, IN (US); Eduard Hendricus Schlarmann, Bergen op Zoom (NL); Gaylord Michael Kissinger, Evansville, IN (US)

(73) Assignee: General Electric Company, Schenectady, NY (US)

( * ) Notice: Subject to any disclaimer, the term of this patent is extended or adjusted under 35 U.S.C. 154(b) by 286 days.

(21) Appl. No.: 09/681,527

(22) Filed: Apr. 24, 2001

(65) Prior Publication Data

US 2003/0017935 A1 Jan. 23, 2003

(51) Int. Cl.$^7$ .................................................. B01J 38/52
(52) U.S. Cl. ........................................ 502/33; 502/56
(58) Field of Search .............................. 502/22, 27, 29, 502/28, 33, 31, 56

(56) References Cited

U.S. PATENT DOCUMENTS

| | | | |
|---|---|---|---|
| 4,051,079 A | | 9/1977 | Melby |
| 4,391,997 A | * | 7/1983 | Mendiratta .................. 568/727 |
| 4,427,829 A | | 1/1984 | Ohara et al. |
| 4,443,635 A | | 4/1984 | McLaughlin |
| 5,008,470 A | * | 4/1991 | Powell et al. ............... 568/727 |
| 5,455,282 A | | 10/1995 | Berg et al. |
| 5,502,016 A | | 3/1996 | Kiedik et al. |
| 5,777,180 A | | 7/1998 | June et al. |

FOREIGN PATENT DOCUMENTS

| | | |
|---|---|---|
| DE | 26 42 596 | 9/1976 |
| GB | 1 565 667 | 4/1980 |
| JP | 57-75146 | 5/1982 |
| JP | 6-92889 | 4/1994 |
| JP | 8-323210 | 12/1996 |
| JP | 10174880 | 12/1996 |

OTHER PUBLICATIONS

Disclosure No. 36908 "Research of Ion Exchange Resins" (Research Disclosures, Jan. 1995, p. 12).

International Search Report Dated Jul. 8, 2002.

Abstract of Japanese Patent JP10174880 Jun. 30, 1998.

* cited by examiner

*Primary Examiner*—Stanley S. Silverman
*Assistant Examiner*—Edward M. Johnson

(57) ABSTRACT

A method for regenerating deactivated sulfonated cation exchange catalysts comprises washing the deactivated catalyst with phenol-water mixtures comprising about 5–20 wt. % of water in phenol at a temperature of about 70–95° C.

9 Claims, No Drawings

REGENERATION OF CATALYSTS USED IN THE MANUFACTURE OF BISPHENOLS

BACKGROUND OF INVENTION

The present disclosure relates to methods for the efficient manufacture of bisphenols. In particular, the present disclosure relates to methods for the regeneration of the ion exchange catalysts commonly used in the manufacture of bisphenols.

Bisphenols are used as raw materials in the preparation of chemical products such as epoxy resins and polycarbonates. They are commonly prepared by the condensation of phenols and ketones. 2,2-Bis(4-hydroxyphenyl) propane (also known as bisphenol A, hereafter "BPA") is among the most important of the bisphenols. It is well known that BPA can be produced by reacting acetone (also known as dimethyl ketone, hereafter "DMK") and phenol in the presence of an acid. Often, an additional co-catalyst is used in the reaction.

A number of acidic catalysts can be used in bisphenol production processes. In recent years, acidic cation exchange resins have come to predominate, strongly acidic, sulfonated polystyrene ion exchange resins being particularly useful. However, some of these acidic catalysts have shown a tremendous proclivity for rapid deactivation. There are many possible reasons for deactivation, including catalyst poisoning with, for example, metals present in the reaction feeds. Additionally, thermal perturbations can cause a loss of the acidic functional groups from the resins on which they are bound. A major factor is the presence of bisphenolic tars and other reaction by-products which, in some cases, build up inside the catalyst bead. Replacing the catalyst is expensive, requires significant labor under adverse conditions, and creates chemical wastes that must be properly disposed of.

Numerous prior art methods are directed to preventing catalyst poisoning. Japanese Patent Publication 6-92889 of Apr. 5, 1994 to Nakawa et al. discloses a process for producing BPA by the condensation of DMK and phenol in which the concentration of methanol in the DMK feed is maintained below 10,000 ppm in order to prevent catalyst poisoning. U.S. Pat. No. 5,777,180 similarly discloses removal of alkyl alcohols from the reactant feed stream also to prevent poisoning the catalyst.

Other approaches are directed to regenerating deactivated catalysts. Japanese Patent Publication 57-075146 assigned to Mitsubishi discloses treating deactivated mercaptopyridyl catalysts with a mercaptan, while Japanese Patent 83-23210 assigned to Chiyoda Corp. discloses treating a deactivated catalyst with a phenol solution containing mercaptoamines. Other methods for regenerating sulfonated ion exchange catalysts used in the manufacture of bisphenol A require multi-step washing procedures with corrosive agents or solutions. For example, Disclosure No. 36908 (Research Disclosures, January 1995, p. 12) teaches a four-step procedure including washing with 1–15 weight percent (wt. %) of a strong base, followed by washing with 1–15% of a strong acid. In order to remove color bodies from strong cation exchange resins, U.S. Pat. No. 4,443,635 discloses washing with an aqueous solution having a pH greater than about 8, and comprising about 10–70 wt. % an alkali or ammonia phenate.

Milder conditions are reported in U.S. Pat. No. 4,051,079 to Melby, which discloses regenerating deactivated sulfonated acidic cation exchange resin catalysts by passing an aqueous phenol solution having greater than 90% phenol and containing an acid having a pKa of less than about 3 through the resin. However, the use of an acid significantly complicates the regeneration process because the acid tends to migrate to the inside of the catalyst bead and must be removed before the catalyst bead can be reused to make bisphenol.

Despite the number of methods proposed to promote catalyst regeneration in the production of bisphenols, there nonetheless remains a need in the art for effective, efficient methods that are suitable for large-scale, industrial production processes.

SUMMARY OF INVENTION

A method for regenerating deactivated sulfonated cation exchange catalysts comprises washing the deactivated catalyst with a phenol-water composition consisting essentially of about 5–20 wt. % of water in phenol at a temperature of about 70–95° C., wherein the phenol-water composition is about 5 to about 50 times the weight of the catalyst, and is recirculated for a length of time effective to regenerate the catalyst.

The above-described and other features and advantages will be appreciated and understood by those skilled in the art from the following detailed description, drawings, and appended claims.

BRIEF DESCRIPTION OF DRAWINGS

Not Applicable

DETAILED DESCRIPTION

A method for regenerating deactivated sulfonated ion exchange catalysts comprises washing the deactivated catalyst with about 5 to about 50 times the weight of the catalyst of a recirculating phenol-water composition consisting essentially of about 5–20 wt. % of water in phenol at a temperature of about 70–95° C. Recirculating the wash composition through the deactivated catalyst bed allows for effective regeneration of the catalyst with significantly lower quantities of wash composition, thereby leading to significant savings for industrial scale processes.

In general, the catalysts are sulfonated aromatic acidic resins comprising hydrocarbon polymers having a plurality of pendant sulfonic acid groups. The pendant sulfonic acid groups are typically 2–4% divinyl benzene crosslinked. Sulfonated polystyrene, poly(styrenedivinylbenzene) copolymer, and sulfonated phenolformaldehyde resins have utility in this regard. Preferably the catalyst is a sulfonated polystyrene cross-linked with 2–4% divinyl benzene. A number of sulfonated polystyrene resin catalysts are commercially available, for example from Rohm and Haas under the trade name Amberlyst 31 or Amberlyt 131 and from Bayer Chemical Company under the trade name K1131. The exchange capacity of the acidic resin is preferably at least about 2.0 milliequivalents (meq.) of hydrogen ion ($H^+$) per gram of dry resin. Ranges from about 3.0 to about 5.5 meq $H^+$ per gram of dry resin are most preferred.

Co-catalysts may also be used, and generally comprise alkyl mercaptans such as methyl mercaptan, ethyl mercaptan, and propyl mercaptan. Methyl mercaptan is presently the preferred co-catalyst.

Phenols suitable for use in regenerating deactivated sulfonated ion exchange catalysts are the same as those used in preparing bisphenols. Useful phenols have a reactive hydrogen preferably in the para-position relative to the phenolic hydroxyl groups. Such phenols may be substituted by one or more alkyl groups such as lower alkyl groups, e.g., methyl, ethyl or tertiary butyl groups, halogen atoms such as chlorine atoms, or other substituents which do not interfere with the carbonyl condensation reaction. Exemplary phenols include ortho- and meta-cresol; 2,6-dimethylphenol ortho-sec. butylphenol; 1,3,5 xylenol; tetramethylphenol; 2-methyl-6-tert.butylphenol, orthophenylphenol; ortho- and meta-chlorophenol, ortho-bromophenol; and 2,6-dichlorophenol. Most preferred is phenol. The phenol employed in regenerating the catalyst may be the same as or different from the phenol used for bisphenol synthesis. Preferably the phenol in regeneration is the same as the phenol in synthesis.

The carbonyl compounds used in the preparing bisphenols may be aldehydes, but preferably are ketones. Specific ketones include acetone, methyl ethyl ketone, methyl propylketone, methyl vinyl acetone, and especially acetophenone and cyclohexanone. Particularly preferred is acetone (DMK).

The phenol/water mixture comprises an effective amount of water in the phenol, generally at least about 5 wt. % based on the total amount of the wash composition. The maximum amount of water is determined to be slightly less than that amount at which the mixture is no longer effective, which can be determined routinely on a case-by-case basis and varies with the identity of the phenol. A convenient maximum is about 20 wt. % of water, based on the total weight of the wash composition. At higher proportions of water, the mixture is no longer one phase at room temperature. The preferred proportions are from about 5 to about 17 weight percent water, based on the total weight of the wash composition.

In contrast to the teaching of the prior art, in particular U.S. Pat. No. 4,051,079 to Melby, the phenol/water mixture need not be acidified in order to be effective. This results in a more economical and efficient procedure due to the fact that there is no acid to be removed from the catalyst beads, and prevents further corrosion and wear of the equipment.

Any temperature above the freezing point of the phenol/water mixture, and below the boiling point of water, can be used, although preferably the temperature of the phenol/water mixture is maintained in the range from about 70 to about 90° C.

In practice, the cation exchange resins are in the form of large beds within tanks. Preferably, the catalyst remains in place during regeneration. Regeneration of the deactivated catalyst accordingly comprises contacting the above described phenol/water mixture through the bed of the deactivated acidic cation exchange resin. Importantly, the inventors hereof have discovered that the volume of wash composition may be minimized by recirculation of the composition, without compromising the effectiveness of the regeneration procedure. Accordingly, the total weight of phenol/water wash composition may by limited to about 5 to about 50 times the weight of catalyst being washed and preferably is about 20 to about 50 times the weight of the catalyst being washed.

All or part of the wash effluent is recirculated in order to conserve the phenol/water mixture. The rate at which the phenol/water mixture is passed through the resin bed is typically in the range from 0 to about 2 weighted hourly space velocities (WHSV). The rate and length of recirculation time effective to regenerate the catalyst will depend on the extent of contamination, and the configuration of the bed, and are readily determined by one of ordinary skill in the art. In general, the recirculation is effective to improve the catalyst activity (as measured by the improvement in the acetone conversion under normal operating conditions) by at least about 4%, preferably about 6%, and most preferably more than about 9%.

A preliminary phenol wash of the resin bed can optionally be used to increase the effectiveness of the regeneration. This will remove some tars, and will reduce the total amount of phenol/water mixture required. A final phenol wash may be optionally used to dry the resin and to remove any free acid tars.

In particular the method for regenerating deactivated sulfonated ion exchange catalysts preferably comprises feeding the resin bed with the phenol/water mixture and measuring the phenol to water ratio as it exits the resin bed. The resin bed typically absorbs water (hydrates) from the phenol/water mixture and so after the phenol/water mixture exits the resin bed, water must be added in order to maintain the desired amount of water in the phenol/water mixture. The mixture is then recirculated and fed into the resin bed again. This process is repeated until the amount of water in the phenol/water mixture going into the resin bed and exiting the resin bed is the same and the desired amount of water in the phenol/water mixture.

The invention is further illustrated by the following non-limiting examples.

EXAMPLE 1

A bed comprising about 30 tons of a sulfonated polystyrene catalyst commercially available under the trade name Amberlyst 131 (a product of Rohm and Haas), and having a titratable acidity of about 5 meq. $H^+$/gram when fresh, was left on stream in a BPA production process. The BPA production process employed 3-mercapto proprionic acid as a bulk promoter and used 4.5 wt. % of acetone in phenol as the reactant feed source.

In order to determine the effectiveness of catalyst regeneration, the quantity of product (BPA) and acetone in the effluent was determined for the fresh catalyst, and after running for 3 days at 70° C. The catalyst was then regenerated by washing the resin bed with a phenol/water mixture (comprising 10 wt. % water) for 24 hours at 70° C., as a rate of 1.6 WHSV without recirculation. Reaction was then restarted and the quantity of BPA and acetone in the effluent as measured. Results are shown in Table 1 below:

TABLE 1

|  | BPA in Effluent, Wt. % | Acetone in Effluent, Wt. % |
| --- | --- | --- |
| Fresh Catalyst | 11.1–11.3 | 0.79–0.84 |
| Before Regeneration | 8.9 | 1.37 |
| After Regeneration | 10.3 | 1.08 |

As may be seen from Table 1, regeneration of the catalyst results in significant improvement in the amount of product produced.

EXAMPLES 2–10

In each of Examples 2–10, 30 grams of a catalyst bed was removed from a production size catalyst bed as described in Example 1 which had been running more than six months. This catalyst was used in laboratory scale experiments to determine the effectiveness of catalyst regeneration. The effectiveness of catalyst regeneration was measured by the acetone conversion percentage (the amount of acetone converted to BPA/amount of acetone employed). As seen in Table 2, varying regeneration conditions were employed. When recirculation was used, the hydration conditions are included. Examples 9 and 10 use fresh catalyst, employ no regeneration and are provided as control examples.

TABLE 2

| No. | Catalyst Sample | Regeneration Parameters | | | Hydration Conditions | Regeneration Conditions | Acetone Conversion (%) before regeneration | Acetone conversion (%) after regeneration | Difference in Acetone Conversion |
|---|---|---|---|---|---|---|---|---|---|
| | | Recirculation | $H_2O$ (Wt. %) | Temperature. (° C.) | | | | | |
| 2 | A131 | No | 10 | 70 | — | WHSV = 0.28; 238 hrs | 78.7 | 89.6 | 11.9 |
| 3 | A131 | Yes | 10 | 95 | WHSV = 1.0 9.5 hrs | WHSV = 0.31 25 hrs | 68.0 | 73.5 | 5.5 |
| 4 | A131 | No | 10 | 95 | — | WHSV = 0.33 24 hrs | 69.0 | 71.4 | 2.4 |
| 5 | A131 | No | 17 | 95 | — | WHSV = 0.27 24 hrs | 65.7 | 75.9 | 10.2 |
| 6 | A131 | Yes | 17 | 95 | WHSV = 1.0 12.5 hours | WHSV = 0.27 24 hrs | 68.6 | 78.2 | 9.6 |
| 7 | A131 | Yes | 5 | 95 | WHSV = 1.0 13 hours | WHSV = 0.31 24 hrs | 70.2 | 73.9 | 3.7 |
| 8 | A131 | Yes | 10 | 95 | WHSV = 1.0 12 hours | WHSV = 0.06 120 hrs | 71.8 | 80.1 | 8.3 |
| 9* | A-131 FRESH | — | — | — | — | — | 88.4 | — | — |
| 10* | A-131 FRESH | — | — | — | — | — | 91.1 | — | — |

*Control Examples

As may be seen by reference to the above Table 2, regeneration with recirculation is a highly successful process and can increase the acetone conversion percentage by as much as 9.6%.

While preferred embodiments have been shown and described, various modifications and substitutions may be made thereto without departing from the spirit and scope of the invention. Accordingly, it is understood that the present invention has been described by way of illustrations and not limitation.

What is claimed is:

1. A method far the regeneration of a deactivated sulfonated ion exchange resin catalyst used in the production of bisphenols, comprising
    contacting the deactivated ion exchange resin with a phenol/water composition which is not acidified and consists essentially of about 5 to about 20 wt % of water at a temperature from about 70 to about 90° C.; and
    recirculating the phenol/water composition for a time effective to regenerate the sulfonated ion exchange resin catalyst.

2. The method of claim 1, further comprising contacting the deactivated ion exchange resin with phenol prior to contacting with the phenol/water composition.

3. The method of claim 1, further comprising contacting the resin with phenol after contacting with the phenol/water composition.

4. The method of claim 1, wherein the phenol/water composition consists essentially of about 5 to about 17 wt. % of water.

5. The method of claim 1, wherein the weight of the phenol/water composition is from about 5 to about 50 times the weight of the resin.

6. The method of claim 5, wherein the weight of the phenol/water composition is from about 20 to about 50 times the weight of the resin.

7. The method of claim 1, wherein the phenol/water composition is contacted with the resin at a flow rate in the range from 0 to about 2 WHSV.

8. The method of claim 1, wherein the regenerated sulfonated ion exchange resin catalyst has an acetone conversion percentage at least 4% higher than the acetone conversion prior to regeneration.

9. A method for the regeneration of a deactivated sulfonated ion exchange resin catalyst used in the production of bisphenols, comprising
    contacting the deactivated ion exchange resin with phenol;
    contacting the deactivated ion exchange resin with a phenol/water composition which is not acidified and consists essentially of about 5 to about 20 wt. % of water, at a temperature from about 70 to about 90° C.; and
    recirculating the phenol/water composition for a time effective to regenerate the catalyst.

* * * * *